(12) United States Patent
Jennewein et al.

(10) Patent No.: US 11,168,105 B2
(45) Date of Patent: Nov. 9, 2021

(54) PROCESS FOR PURIFICATION OF NEUTRAL HUMAN MILK OLIGOSACCHARIDE USING SIMULATED MOVING BED CHROMATOGRAPHY

(71) Applicant: JENNEWEIN BIOTECHNOLOGIE GMBH, Rheinbreitbach (DE)

(72) Inventors: Stefan Jennewein, Bad Honnef (DE); Markus Helfrich, Bad Hoenningen (DE)

(73) Assignee: JENNEWEIN BIOTECHNOLOGIE GMBH, Rheinbreitbach (DE)

( * ) Notice: Subject to any disclaimer, the term of this patent is extended or adjusted under 35 U.S.C. 154(b) by 80 days.

(21) Appl. No.: 16/440,100

(22) Filed: Jun. 13, 2019

(65) Prior Publication Data

US 2019/0292211 A1  Sep. 26, 2019

Related U.S. Application Data

(63) Continuation of application No. 15/027,047, filed as application No. PCT/EP2014/071145 on Oct. 2, 2014, now Pat. No. 10,435,427.

(30) Foreign Application Priority Data

Oct. 4, 2013 (EP) .................................. 13187369

(51) Int. Cl.
*C07H 3/06* (2006.01)
*A23L 33/00* (2016.01)
(Continued)

(52) U.S. Cl.
CPC ................ *C07H 3/06* (2013.01); *A23L 33/10* (2016.08); *A23L 33/40* (2016.08); *A61K 31/702* (2013.01);
(Continued)

(58) Field of Classification Search
None
See application file for complete search history.

(56) References Cited

U.S. PATENT DOCUMENTS 5,576,040 A  11/1996 Moller et al.
6,454,946 B1  9/2002 DeFrees
(Continued)

FOREIGN PATENT DOCUMENTS

CN  1242776 A  1/2000
CN  103025749 A  4/2013
(Continued)

OTHER PUBLICATIONS

Yu: Utilization of major fucosylated and sialylated human milk oligosaccharides by isolated human gut microbes; Glycobiology, vol. 23, Issue 11, Nov. 1, 2013, pp. 1281-1292, https://doi.org/10.1093/glycob/cwt065; Published: Sep. 7, 2013) (Year: 2013).*
(Continued)

*Primary Examiner* — Patricia A George
(74) *Attorney, Agent, or Firm* — McBee Moore & Vanik IP, LLC

(57) ABSTRACT

The present application discloses a process for the purification of a neutral human milk oligosaccharide (neutral HMO). The process uses simulated moving bed (SMB) chromatography which allows the continuous purification of large quantities of HMOs with high purity. Contrary to chemical synthesis routes of neutral HMOs, and their subsequent purification, the presented process allows the provision of HMOs free of noxious chemicals, such as e.g. trace amounts of heavy metals or organic solvents. The individual neutral HMO product may be obtained in solid form by spray drying or as a concentrated syrup. The provided neutral HMO is very well-suited for use in food applications.

20 Claims, 12 Drawing Sheets

(51) Int. Cl.
    *A61K 31/702*     (2006.01)
    *A23L 33/10*     (2016.01)
    *B01D 15/18*     (2006.01)
    *C07H 1/08*     (2006.01)

(52) U.S. Cl.
    CPC ............. *B01D 15/185* (2013.01); *C07H 1/08* (2013.01); *A23V 2002/00* (2013.01)

(56) References Cited

U.S. PATENT DOCUMENTS

| | | |
|---|---|---|
| 6,936,173 B2 | 8/2005 | DeFrees |
| 9,453,230 B2 | 9/2016 | Merighi et al. |
| 2012/0116065 A1 | 5/2012 | Dekany et al. |
| 2012/0294840 A1 | 11/2012 | Newburg et al. |

FOREIGN PATENT DOCUMENTS

| | | |
|---|---|---|
| EP | 2272522 B1 | 9/2017 |
| JP | H02-286695 A | 11/1990 |
| JP | H06-253879 A | 9/1994 |
| JP | 2008-61531 A | 3/2008 |
| RU | 2007110174 A | 9/2008 |
| WO | 2006/018314 A2 | 2/2006 |
| WO | 2009151330 A1 | 12/2009 |
| WO | 2010-115934 A1 | 10/2010 |
| WO | 2010/115935 A1 | 10/2010 |
| WO | 2011/150939 A1 | 12/2011 |
| WO | 2012/076321 A1 | 6/2012 |
| WO | 2012/158517 A1 | 11/2012 |
| WO | 2012156898 A1 | 11/2012 |
| WO | 2012160080 A1 | 11/2012 |
| WO | 2013185780 A1 | 12/2013 |

OTHER PUBLICATIONS

MF: Martinez-Ferez: Recovery of caprine milk oligosaccharides with ceramic membranes; Journal of Membrane Science 276 (2006) 23-30; available online Oct. 10, 2005 (Year: 2005).*
Davis: WO2013032674; published Mar. 7, 2013. (Year: 2013).*
Katsumi: Neutral Origosaccharide-Containing Nersery Formulated Milk; JP 2003-047402, published Feb. 18, 2003 (Year: 2003).*
German: Human Milk Oligosaccharides: Evolution, Structures and Bioselectivity as Substrates for Intestinal Bacteria; Copyright © 2008 Nestec Ltd. (Year: 2008).*
Geisser: Separation of lactose from human milk oligosaccharides with simulated moving bed chromatography; Journal of Chromatography A, 1092 (2005) 17-23 (Year: 2005).*
Geisser, A. et al, "Separation of lactose from human milk oligosaccharides with simulated moving bed chromatography", Journal of Chromatography, vol. 1092, No. 1, p. 17-23, Oct. 21, 2005.
Kuhn, Richard et al, "Kristallisierte Fucosido-Lactose", Chemische Berichte, vol. 89, No. 11, p. 2513, Nov. 1, 1956.
Wright: The Bacteriological Screening of Donated Human Milk: Laboratory Experience of British Paediatric Association's Published Guidelines; Journal of Infection (1998) 3@ 23-27 (Year: 1998).
Han: Biotechnological production of human milk oligosaccharides; Biotechnology Advances 30 (2012) 1268-1278 (Year: 2012).
Donald: Separation of human milk oligosaccharides by recycling chromatography. First isolation of lacto-N-neo-difucohexaose II and 3'-galactosyllactose from this source; Carbohydrate Research, vol. 178, Issue 1, Jul. 15, 1988, pp. 79-91. (Year: 1988).
Katsumi: Neutral Origosaccharide-Containing Nersery Formulated Milk; JP,2003-047402,A, published Feb. 18, 2003. (Year: 2003).
Keogh: Effect of the particle size of spray-dried milk powder on some properties of chocolate; INRA Editions, 2004, 84 (4), pp. 375-384. (Year: 2004).
Yu: Utilization of major fucosylated and sialylated human milk oligosaccharides by isolated human gut microbes; Glycobiology, vol. 23, Issue 11, Nov. 1, 2013, pp. 1281-1292, http://doi.org/10.1093/glycob/cwt065; Published: Sep. 7, 2013 (Year: 2013).
Manenda: Separation of Bioactive Peptides by Electrodialysis with Ultrafiltration Membranes: Dissertation presented to University of Lisbon, Jul. 2013.
Search Report of Russian Patent Application No. 2016109548/04(015034).
Third-Party Observation for application No. EP 20130187369 dated Sep. 6, 2017.
Extended Search Report of European Patent Application No. 13187369.7 dated Nov. 28, 2013.
International Preliminary Report on Patentability and Written Opinion of International Application No. PCT/EP2014/071145 dated Apr. 14, 2016.
Third Party Observation for application No. EP 20130187369 dated Mar. 26, 2019.
Decision to Grant of Russian Application No. 2016109548/04 dated Feb. 28, 2019.
Decision of Rejection of Korean Application No. 201480054230.4 dated Feb. 11, 2019.
Third Party Observation for Application No. EP20130187369, dated Apr. 14, 2020.
Third Party Observation for application No. EP 13187369.7 dated Jul. 12, 2019.
Third Party Observation for application No. EP 14777665.2 dated Jul. 12, 2019.

\* cited by examiner

PROCESS FOR PURIFICATION OF NEUTRAL HUMAN MILK OLIGOSACCHARIDE USING SIMULATED MOVING BED CHROMATOGRAPHY

CROSS-REFERENCE TO RELATED APPLICATIONS

This application is a Continuation of U.S. patent application Ser. No. 15/027,047, filed 4 Apr. 2016, which is a National Stage entry of International Application No. PCT/EP2014/071145, filed 2 Oct. 2014, which claims priority to European Patent Application No. 13187369.7, filed 4 Oct. 2013. The disclosure of the priority applications are incorporated in their entirety herein by reference.

The present application discloses a process for the purification of a neutral human milk oligosaccharide (neutral HMO). The process uses simulated moving bed (SMB) chromatography which allows the continuous purification of large quantities of HMOs with high purity. Contrary to chemical synthesis routes of neutral HMOs, and taheir subsequent purification, the presented process allows the provision of HMOs free of noxious chemicals, such as e.g. trace amounts of heavy metals or organic solvents. The individual neutral HMO product may be obtained in solid form by spray drying or as a concentrated syrup. The provided neutral HMO is very well-suited for use in food applications.

Human milk represents a complex mixture of carbohydrates, fats, proteins, vitamins, minerals and trace elements. By far the most predominant fraction is represented by carbohydrates, which can be further divided into lactose and more complex oligosaccharides. Whereas lactose is used as an energy source, the complex oligosaccharides are not metabolized by the infant. The fraction of complex oligosaccharides accounts for up to $\frac{1}{10}$ of the total carbohydrate fraction and consists of probably more than 150 different oligosaccharides. The occurrence and concentration of these complex oligosaccharides are specific to humans and thus cannot be found in large quantities in the milk of other mammals, such as for example domesticated dairy animals.

The existence of these complex oligosaccharides in human milk has been known already for a long time and the physiological functions of these oligosaccharides have been subject to medical research for many decades. For some of the more abundant human milk oligosaccharides, specific functions have already been identified.

The limited supply and difficulties of obtaining pure fractions of individual HMOs led to the development of chemical routes to some of these complex molecules. However, synthesis of HMOs by chemical synthesis, enzymatic synthesis or fermentation has proved to be challenging. At least large-scale quantities as well as qualities adequate for food applications have not been able to be provided to date. In this regard, particularly chemical synthetic routes of specific HMOs (e.g. the HMO 2'-fucosyllactose; see WO 2010/115935 A1) involve several noxious chemicals, which involve the risk of contamination of the final product.

Due to the challenges involved in the chemical synthesis of human milk oligosaccharides, several enzymatic methods and fermentative approaches have been developed. However, these methods yield complex mixtures of oligosaccharides i.e. the desired product is contaminated with starting material such as lactose, biosynthetic intermediates and substrates such as individual monosaccharides and polypeptides etc.

Processes in the state of the art for purifying individual oligosaccharide products from these complex mixtures are technically complex and also uneconomical for food applications. For the purification of the disaccharides lactose or sucrose from complex mixtures such as whey or molasses, industrial scale processes have been developed which involve multiple crystallizations. The disadvantage of said methods is that they are elaborate and only lead to low yields.

For the purification of complex oligosaccharides, such as certain HMOs, gel-filtration chromatography has been the method of choice until now. The disadvantage of gel-filtration chromatography is that it cannot be efficiently scaled up and it is unsuitable for continuous operation. Thus, gel-filtration chromatography is not economical and renders it impossible to provide certain HMOs—like the HMO 2'-fucosyllactose—in reasonable amounts and quality to use them in human food.

Simulated moving bed (SMB) chromatography has its roots in the petrochemical and mineral industries. Today, SMB chromatography is used by the pharmaceutical industry for the separation of enantiomers from racemic mixtures. SMB chromatography has already been used for the separation of the monosaccharide fructose from fructose-glucose solutions and for the separation of the disaccharide sucrose from sugar beet or sugar cane syrups on large-scale. However, SMB chromatography has not yet been used for the purification of HMOs, or any other complex oligosaccharide, from fermentations yet.

Simulated moving bed (SMB) chromatography was developed as a continuous separation process analogous to continuous chemical separation processes such as rectification. In rectification, a countercurrent is established between the liquid and the gaseous phase, which allows then the continuous application of feed and withdrawal of product(s). In addition, counter-current chromatographic operations in theory should achieve separations superior to conventional cross-current operations. However, chromatographic counter-current operations would require the mobile and stationary phases to move in opposite directions. Thus, SMB chromatography was developed as a practical solution to the difficulties related to the concept of moving solid chromatography material in a continuous chromatographic separation process.

The standard SMB concept involves four different zones with four externally applied streams: a feed stream comprising the components to be separated, a desorbent or mobile phase stream, an extract and a raffinate stream (with the raffinate stream representing the less retained component(s)). These liquid streams divide the SMB system into four different zones (each zone or section can comprise one or more columns) with the following tasks: zone I is required for the regeneration of the solid phase, the purpose of zone II is the desorption of the less strongly desorbed material, the task of zone III is the adsorption of the strongly adsorbed material and finally the task of zone IV is the adsorption of the less adsorptive material. Thus, more strongly adsorbing components establish a concentration wave in zone II and are transported to the extract port whereas less strongly adsorbing components migrate towards the raffinate port.

In principle, zone I and IV serve for regeneration of the solid phase (regeneration zones) whereas zones II and III can be regarded as the actual separation zones of the system (separation zones). In addition to the four liquid streams and resulting zones, the system contains (for the closed loop operation) a recycling pump for the mobile phase (desorbent), passing the mobile phase through the fixed zones in one direction. Counter-current flow is then achieved by the periodical shifting and continuous supply or withdrawal of feed, desorbent and products sequentially from one column to the next in the system.

Besides the standard closed loop, 4 zone SMB system, open loop, 3 zone systems can be used as well. The 3 zone open loop systems are economical in the case where fresh solvent is rather inexpensive e.g. where water or water/ethanol is used as mobile phase. By using a 3 zone open loop configuration, the regeneration of the liquid phase is no longer needed, thus making zone IV obsolete.

Besides the standard SMB systems for the separation of a two component mixture also eight-zone closed loop or five zone open loop SMB systems have been developed for the separation of more than 2 components.

Due to the continuous mode of operation and also the possibility of using rather larger column sizes and recycling of the mobile phase, the SMB system can in principle be scaled into production volumes of 100 s of tons.

Starting from this prior art, the technical problem is the provision of a novel process to provide a neutral HMO in large amounts, with high purity and free of noxious chemicals.

The technical problem is solved by the process according to claim 1, the neutral HMO according to claim 14 and the use of a neutral HMO according to claim 18. The dependent claims display advantageous embodiments.

Figure 1:
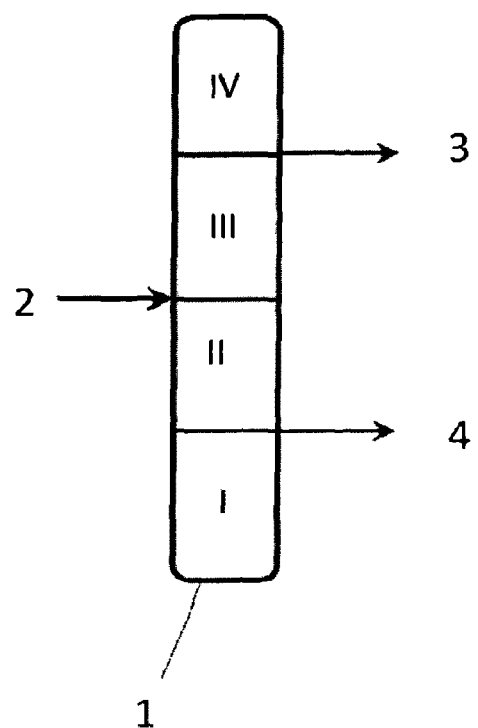
FIG. 1 schematically illustrates one purification step using simulated moving bed chromatography.

The present invention provides a process for purification of a neutral HMO (e.g. 2'-fucosyllactose) in a continuous chromatography (or in a continuous manner) from a crude solution comprising the neutral HMO (e.g. 2'-fucosyllactose) and contaminants, wherein the crude solution comprising the neutral HMO (e.g. 2'-fucosyllactose) and contaminants comprises or consists of a solution which is selected from the group consisting of microbial fermentation extract, biocatalysis reaction solution, chemical synthesis solution, and combinations thereof and wherein the purity of the neutral HMO (e.g. 2'-fucosyllactose) in the solution is <80%. The process is characterized in that the crude solution is applied to at least one purification step using simulated moving bed chromatography. In this way, a purified solution comprising the desired neutral HMO (e.g. 2'-fucosyllactose) with a purity of 80% is provided.

The process for purification of a neutral HMO in a continuous chromatography may be a process for purification of a neutral HMO in a continuous manner. In this regard, the neutral HMO may be 2'-fucosyllactose or lacto-N-tetraose.

The Applicant has discovered that with the developed process involving a purification step using simulated moving bed chromatography, HMOs may be provided with high purity, without heavy metal contaminants and in a continuous manner. Thus, large amounts of high-quality HMOs may be provided in a very convenient and economical way, e.g. from a crude solution from microbial fermentation. The inventive process also turned out to be highly stable even without a step of regeneration of the column material (e.g. cationic column material) used in the simulated moving bed chromatography step. In fact, the whole process can be operated in a stable and continuous manner for several months.

In a preferred embodiment, the purity of the neutral HMO in the crude solution is ≤70%, ≤60%, ≤50%, ≤40%, ≤30%, ≤20%, ≤10% or ≤5% and/or the purified solution contains the HMO with a purity of ≥80%, preferably of ≥90%. The term "crude solution" refers to a solution containing neutral HMO before the purification step of single moving bed chromatography whereas the purified solution refers to a solution after the step of single moving bed chromatography.

The at least one simulated moving bed chromatography step may have i) at least 4 columns, preferably at least 8 columns, more preferably at least 12 columns, wherein at least one column comprises a weak or strong cation exchange resin, preferably a cation exchange resin in the $H^+$-form or $Ca^{2+}$-form; and/or ii) four zones I, II, III and IV with different flow rates; and/or iii) an eluent comprising or consisting of water, preferably ethanol and water, more preferably 5-15 vol.-% ethanol and 85-95 vol.-% water, most preferably 9-11 vol.-% ethanol and 89-91 vol.-% water, wherein the eluent optionally further comprising sulphuric acid, preferably ≤10 mM sulphuric acid; more preferably ≤2-5 mM sulphuric acid; and/or iv) an operating temperature of 15° to 60° C., preferably 20° to 55° C., more preferably 25° to 50° C.

If the HMO to be purified is 2'-fucosyllactose, the at least one simulated moving bed chromatography step may have i) four zones I, II, III and IV with different flow rates, wherein the flow rates are preferably: 28-32 ml/min in zone I, 19-23 ml/min in zone II, 21-25 ml/min in zone III and/or 16-20 ml/min in zone IV; and/or ii) a feed rate of 2-4 ml/min, preferably 3 ml/min; and/or iii) an eluent flow rate of 10-13 ml/min, preferably 11.5 ml/min; and/or iv) a switching time of 16-20 min, preferably 17-19 min, more preferably 18 min.

Preferably, at least one of the columns comprises 0.1 to 5000 kg of cation exchange resin, preferably 0.2 to 500 kg of cationic exchange resin, more preferably 0.5 to 50 kg of cation exchange resin, most preferably 1.0 to 20 kg of cation exchange resin.

Importantly, scaling-up of the amount of cation exchange material, the flow rate in the different zones, the feed rate, the eluent flow rate and/or the switching time is possible. The scaling-up may be by a factor of 2, 3, 4, 5, 6, 7, 8, 9, 10, 20, 30, 40, 50, 60, 70, 80, 90, 100, 1000 or all possible scaling factors in between said values.

In the columns, a strong cation exchange resin may be used as stationary phase. Preferably, the cation exchange resin is a sulfonic acid resin, more preferably a Purolite® PCR833H (Purolite, Ratingen, Germany), Lewatit MDS 2368 and/or Lewatit MDS 1368 resin. If a cation ion exchange resin is employed in the columns, it may be regenerated with sulphuric acid. Sulphuric acid can be employed in the eluent, preferably at concentration of 10 mM sulphuric acid or less. The (strong) cation exchange resin may be present in $H^+$-form or in $Ca^{2+}$-form.

Operating temperatures above 60° C. are not preferred during simulated moving bed chromatography. It was found that especially in the presence of a strong cation ion exchange resin (in $H^+$-form or $Ca^{2+}$-form) as stationary phase, the applied neutral oligosaccharides were significantly destabilized i.e. depolymerized which was detrimental to the final yield of the neutral HMO.

In an advantageous embodiment of the invention, the invention is characterized in that the purified solution is applied to at least one further purification step using simulating moving bed chromatography, wherein a purified solution comprising the neutral human milk oligosaccharide with a purity of ≥90%, preferably ≥92%; more preferably ≥93% is provided. In particular, the invention yields a HMO product free of recombinant DNA, and free of host strain proteins.

The further simulated moving bed chromatography may have
i) at least 4 columns, preferably at least 8 columns, more preferably at least 12 columns, wherein at least one column comprises a weak or strong cation exchange resin, preferably a cation exchange resin in the $H^+$-form or $Ca^{2+}$-form; and/or
ii) four zones I, II, III and IV with different flow rates, and/or
iii) an eluent comprising or consisting of water, preferably ethanol and water, more preferably 5-15 vol.-% ethanol and 85-95 vol.-% water, most preferably 9-11 vol.-% ethanol and 89-91 vol.-% water, wherein the eluent optionally further comprises sulphuric acid, preferably ≤10 mM sulphuric acid; more preferably ≤2-5 mM sulphuric acid, and/or
iv) an operating temperature of 15° to 60° C., preferably 20° to 55° C., more preferably 25° to 50° C.

If the HMO to be purified is 2'-fucosyllactose, the further simulated moving bed chromatography step may have
i) four zones I, II, III and IV with different flow rates, wherein the flow rates are preferably: 28-32 ml/min in zone I, 19-23 ml/min in zone II, 21-25 ml/min in zone III and/or 16-20 ml/min in zone IV; and/or
ii) a feed rate of 2-4 ml/min, preferably 3 ml/min; and/or
iii) an eluent flow rate of 10-13 ml/min, preferably 11.5 ml/min; and/or
iv) a switching time of 16-20 min, preferably 17-19 min, more preferably 18 min.

Particularly, at least one of the columns contains 0.1 to 5000 kg of cation exchange resin, preferably 0.2 to 500 kg of cation exchange resin, more preferably 0.5 to 50 kg of cation exchange resin, most preferably 1.0 to 20 kg of cation exchange resin.

Importantly, scaling-up of the amount of cation exchange material, the flow rate in the different zones, the feed rate, the eluent flow rate and/or the switching time is possible. The scaling-up may be by a factor of 2, 3, 4, 5, 6, 7, 8, 9, 10, 20, 30, 40, 50, 60, 70, 80, 90, 100, 1000 or all possible scaling factors in between said values.

After a purification step using simulated moving bed chromatography, the pH of the purified solution may be adjusted to pH 7, preferably by adding a base, more preferably by adding NaOH (e.g. 0.2 M NaOH).

According to the invention, the crude solution containing the neutral HMO and contaminants comprises or consists of a solution which is selected from the group consisting of microbial fermentation, microbial fermentation extract, biocatalysis reaction solution, chemical synthesis solution and combinations thereof. Fermentation as a source of the neutral HMO has the advantage that it is more cost-effective than chemical synthesis or biocatalysis i.e. enzymatic synthesis. Thus, a microbial fermentation extract is preferred.

Preferably, before applying the solution to the at least one simulating moving bed chromatography step, the solution (preferably a microbial fermentation solution) comprising the neutral HMO is
i) filtered or centrifuged to remove the biomass and/or any insoluble material, preferably filtered with activated carbon, charcoal, celite and/or by cross-flow filtration to remove any insoluble material and organic contaminants, more preferably filtered by cross-flow filtration, most preferably filtered by cross-flow filtration using a microfiltration membrane; and/or
ii) applied to at least one purification step using cation and/or anion exchange chromatography, preferably first at least one cation exchange chromatography step and then at least one anion exchange chromatography step.

In a further preferred embodiment, before applying the solution to at least one purification step using simulated moving bed chromatography or after a purification step using simulated moving bed chromatography, the solution containing the neutral HMO is electrodialysed and/or diafiltered, preferably diafiltered with a nanofiltration membrane, more preferably diafiltrated with a nanofiltration membrane having a size exclusion limit of ≤20 Å. Most preferably, the solution is dialysed to a conductivity of ≤15 mS/cm, preferably ≤10 mS/cm, more preferably ≤5 mS/cm.

If the crude solution is dialysed before applying the solution to at least one purification step using simulated moving bed chromatography, major contaminants depend on the origin of the neutral HMO fractions (i.e. chemical synthesis, biocatalysis or fermentation). Typical contaminants are monosaccharides (e.g. glucose, galactose, fucose, etc.), disaccharides (e.g. lactose) and by-products (e.g. lactulose). In case where fermentation was used as a source of the neutral HMO, the crude solution usually comprises the employed carbon source (e.g. glycerol, sucrose and/or glucose) as well as by-products of the employed microbes (e.g. higher molecular mass oligosaccharides) as contaminants. As further contaminants, also oligosaccharides may be present which are generated due to the promiscuity of the used glycosyltransferases (e.g. glycosyltransferases in the synthesizing cell which convert the desired product, the substrate or an intermediate product into a contaminating oligosaccharide). Said contaminants can efficiently be removed by a purification step using simulated moving bed (SMB) chromatography.

After dialysis, preferably after electrodialysis and/or diafiltration (optionally before applying the solution to the SMB chromatographic process), the solution comprising the HMO may be concentrated, in particular i) to a concentration of ≥50 g/l, ≥100 g/l, preferably ≥200 g/l, more preferably ≥300 g/l; and/or
ii) employing a vacuum concentrator; and/or
iii) by nanofiltration; and/or
iv) at a temperature of 4° to 50° C., preferably 10° to 45° C., optionally 20° to 40° C. or 30° to 35° C.

More preferably, the HMO-comprising fraction is concentrated by employing nanofiltration. The nanofiltration step can be further used to dialyse away contaminating salts. Here, the HMO fraction may firstly be concentrated by nanofiltration and the resulting concentrated HMO fraction is then subsequently diluted with water, preferably double-distilled $H_2O$ (dd$H_2O$) or deionized water, and then the diluted HMO fraction may again be concentrated using a nanofiltration membrane.

Concentration by nanofiltration is particularly preferred because an exposure of the neutral HMOs to high temperatures may be dispensed with. Thus, said method of concentration is less destructive to the structure of HMOs than a heat treatment i.e. it does not induce thermal damage to the neutral HMOs during concentration. An additional advantage of nanofiltration is that it can be used both for concentrating and for dialysing (diafiltering) the neutral HMOs. In other words, a membrane used in nanofiltration does not have to be exchanged if the concentration step and the dialysis step are implemented in succession in the inventive process. In addition, the salt concentration of the solution containing neutral HMOs can be significantly reduced. This saves material and time and makes the whole process more economical. Preferably, nanofiltration is combined with electrodialysis. This combination turned out to give excellent results in concentrating and desalting.

In a preferred embodiment of the invention, the purified solution is sterile filtered and/or subjected to endotoxin removal, preferably by filtration of the purified solution through a 3 kDa filter.

The purified solution may be spray-dried, particularly spray-dried at a concentration of the neutral HMO of 20-60% (w/v), preferably 30-50% (w/v), more preferably 35-45% (w/v), an inlet temperature of 110-150° C., preferably 120-140° C., more preferably 125-135° C. and/or an outlet temperature of 60-80° C., preferably 65-70° C.

In a preferred embodiment of the inventive process, the neutral HMO which is to be purified is a neutral HMO having more than 3 monosaccharide units, preferably a neutral human milk trisaccharide, tetrasaccharide, pentasaccharide or hexasaccharide. More preferably, the neutral HMO is selected from the group consisting of 2'-fucosyllactose, 3-fucosyllactose, 2',3-difucosyllactose, lacto-N-triose II, lacto-N-tetraose, lacto-N-neotetraose, lacto-N-fucopentaose I, lacto-N-neofucopentaose I, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose, lacto-N-neohexaose, para-lacto-N-hexaose, para-lacto-N-neohexaose and difucosyl-lacto-N-neohexaose. Most preferably, the neutral HMO is 2'-fucosyllactose or lacto-N-neotetraose.

Optionally, it is also possible that the neutral HMO is not 2'-fucosyllactose.

In an advantageous embodiment of the invention, the inventive process is characterized in that the crude solution comprising the neutral human milk oligosaccharide and contaminants comprises or consists of a microbial fermentation extract, wherein the microbial fermentation extract is obtained in at least one step of microbial fermentation which is preferably followed by at least one step of a) filtration of a solution, preferably the crude solution, to separate soluble material from insoluble material after the microbial fermentation; and/or
b) ion exchange chromatography, preferably cation exchange chromatography, more preferably cation exchange chromatography followed by anion exchange chromatography, of a solution, preferably of a solution obtained in step a); and/or
c) concentration of a solution, preferably a solution obtained in step b), more preferably by evaporation of water and/or by nanofiltration, optionally by concentrating more than once; and/or
d) dialysis of a solution, preferably of a solution obtained in step c), more preferably by electrodialysis and/or diafiltration, most preferably diafiltration with a nanofiltration membrane, optionally by dialysing more than once; and/or
e) chromatography of a solution using simulated moving bed chromatography, preferably a solution obtained in step d); and/or
f) filtration of a solution, preferably a solution obtained in step e), to separate neutral human milk oligosaccharide from coloured contaminants, more preferably by filtration through activated carbon; and/or
g) spray-drying a purified solution comprising the neutral human milk oligosaccharide, preferably a purified solution obtained in step f).

Most preferably, all steps a) to g) are implemented in succession. The implementation of all steps a) to g) in succession has been found to be the most advantageous embodiment of the inventive process. Said process is cost and time efficient and enables the provision of large quantities of highly pure, spray-dried (i.e. amorphous) neutral HMOs from microbial fermentation (extracts). In particular, the concentration and desalting steps of the HMO solution using nanofiltration represent extremely cost efficient and gentle operating steps preventing undesired by-product formation.

The invention thus provides a neutral HMO which is producible with the inventive process. The neutral HMO (e.g. 2'-fucosyllactose or lacto-N-tetraose) is preferably spray-dried. The purified neutral HMO has the advantage of being highly pure and being free of heavy metal contaminants, and/or organic solvents.

The neutral HMO according to the invention can have
i) a solid granule form; and/or
ii) a glass transition temperature of 60 to 90° C., preferably 62 to 88° C., more preferably 64 to 86° C., determined by differential scanning calorimetry; and/or
iii) a particle size of 5 to 500 µm, preferably 10 to 300 µm, determined by laser diffraction; and/or
iv) a mean particle size of 10 to 100 µm, preferably 20 to 90 µm, more preferably 30 to 80 µm, most preferably 40 to 70 µm, determined by laser diffraction; and/or
v) an amorphous state, preferably an amorphous state with no characteristic peaks of crystalline matter in X-ray powder diffraction, and/or
vi≤) a moisture content of 10%, preferably ≤8%, more preferably <5%.

The neutral HMO may be used in medicine, preferably in prophylaxis or therapy of gastrointestinal disorders. It can also be used in nutrition, preferably medicinal nutrition or dairy nutrition (e.g. cereal products).

In a preferred embodiment of the invention, the neutral human milk oligosaccharide is a neutral HMO having more than 3 monosaccharide units, preferably a neutral human milk trisaccharide, tetrasaccharide, pentasaccharide or hexasaccharide. More preferably, the neutral HMO is selected from the group consisting of 2'-fucosyllactose, 3-fucosyllactose, 2',3-difucosyllactose, lacto-N-triose II, lacto-N-tetraose, lacto-N-neotetraose, lacto-N-fucopentaose I, lacto-N-neofucopentaose I, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose, lacto-N-neohexaose, para-lacto-N-hexaose, para-lacto-N-neohexaose and difucosyl-lacto-N-neohexaose. Most preferably, the neutral HMO is 2'-fucosyllactose or lacto-N-neotetraose.

Optionally, it is also possible that the neutral HMO is not 2'-fucosyllactose.

Furthermore, it is proposed to use the neutral HMO according to the invention as additive in food, preferably as additive in human food and/or pet food, more preferably as additive in human baby food.

With reference to the following Figures and Examples, the subject according to the invention is intended to be explained in more detail without wishing to restrict said subject to the special embodiments shown here.

FIG. 1 schematically illustrates one purification step using simulated moving bed chromatography. The simulated moving bed chromatography may have e.g. 12 columns in a serial arrangement 1, wherein the arrangement is divided into four different zones I, II, III and IV. The crude solution containing the neutral HMO 2'-fucosyllactose and contaminants is applied between zone II and III to the feed entry 2. Extract is removed from exit 4 between zone I and zone II whereas raffinate is removed at exit 3 between zone III and zone IV. Raffinate at exit 3 contains the purified HMO 2'-fucosyllactose whereas extract at exit 4 contains low molecular weight contaminants (e.g. monosaccharides and disaccharides).

Figure 2:
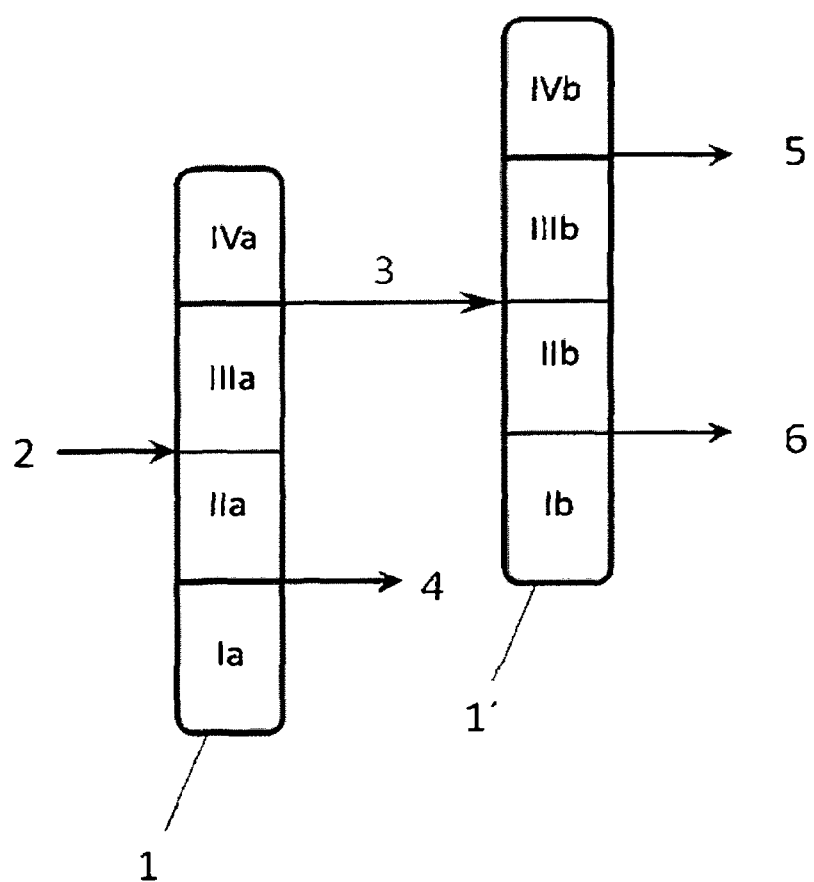
FIG. 2 schematically illustrates two subsequent purification steps using simulated moving bed chromatography.

FIG. 2 schematically illustrates two subsequent purification steps using simulated moving bed chromatography. Each simulated moving bed chromatography may have e.g. 12 columns in a serial arrangement 1, 1', wherein each arrangement is divided into four different zones Ia, IIa, IIIa and IVa or zones Ib, IIb, IIIb and IVb, respectively. The crude solution comprising the neutral HMO 2'-fucosyllactose and contaminants is applied between zone IIa and IIIa of the first arrangement 1 to the feed entry 2. Extract is removed at exit 4 between zone Ia and zone IIa whereas raffinate leaves the first serial arrangement 1 at exit 3 between zone IIIa and zone IVa and is applied to the second serial arrangement 1' between zone IIb and IIIb. In the second serial arrangement 1', extract is removed at exit 6 whereas raffinate is removed at exit 5 between zone IIIb and zone IVb. Raffinate at exit 5 contains highly purified 2'-fucosyllactose whereas extract at exit 6 contains high molecular weight contaminants (e.g. higher oligosaccharides).

Figure 3:
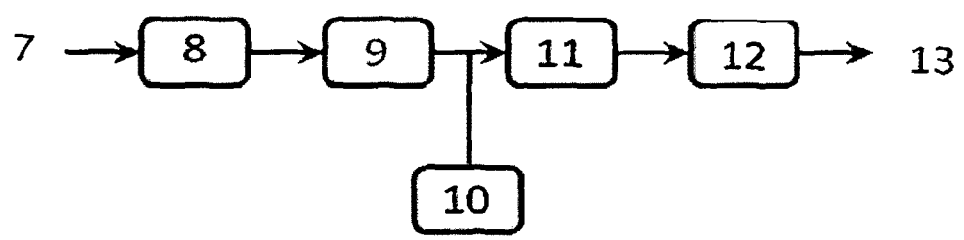
FIG. 3 schematically illustrates a preferred purification scheme according to the present invention.

FIG. 3 schematically illustrates a preferred purification scheme according to the present invention. Firstly, a solution 7 containing the neutral HMO 2'-fucosyllactose and contaminants is applied to an electrodialysis step 8 until a conductivity of ≤0.5 mS/cm is obtained. Said solution is concentrated until the solution has reached a concentration of 2'-fucosyllactose of approx. 40% (w/v). Subsequently, said solution is applied to at least one purification step using simulated moving bed chromatography 9. After the simulated moving bed chromatography, a purified solution comprising 2'-fucosyllactose with high purity is obtained. Said pure solution is subjected to sterile filtration 11 (preferably also endotoxin removal). Before sterile filtration 11, an additional step of electrodialysis 10 with subsequent concentration may optionally be performed. After sterile filtration 11, the purified solution comprising 2'-fucosyllactose is subjected to spray drying 12 and pure, spray dried 2'-fucosyllactose 13 is obtained in solid granule form.

Figure 4:
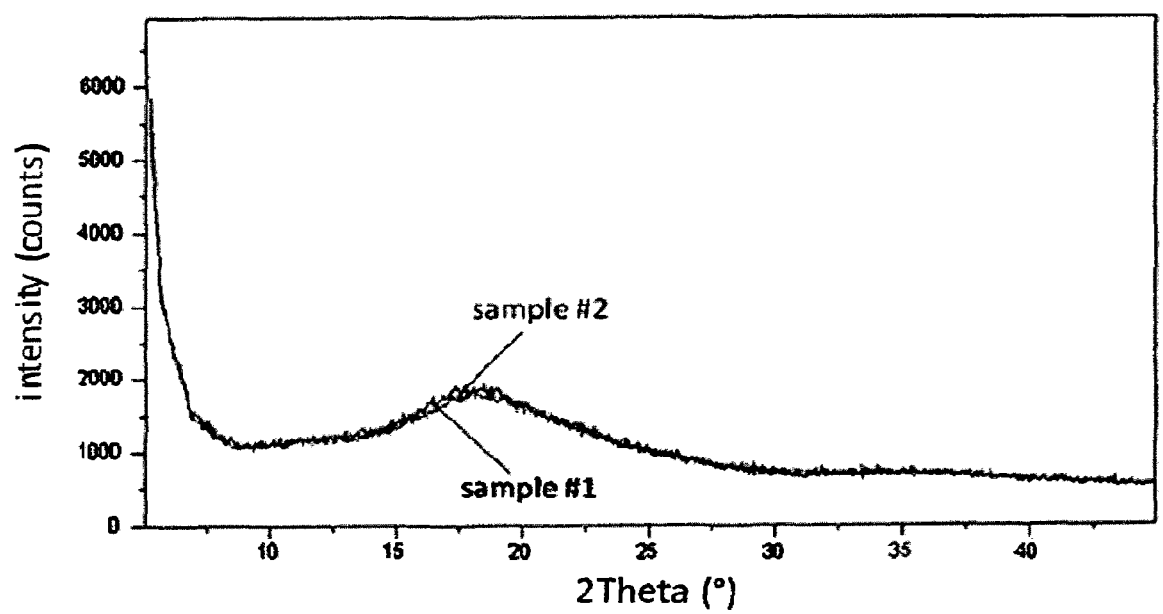
FIG. 4 shows the result of an X-ray powder diffraction analysis of two samples of spray-dried 2'-fucosyllactose according to the present invention.

FIG. 4 shows the result of an X-ray powder diffraction analysis of two samples of spray-dried 2'-fucosyllactose according to the present invention (sample #1 and sample #2). The two obtained diffractograms reveal that both sample #1 and sample #2 are in the fully amorphous state (no characteristic peaks of crystalline matter).

Figure 5:
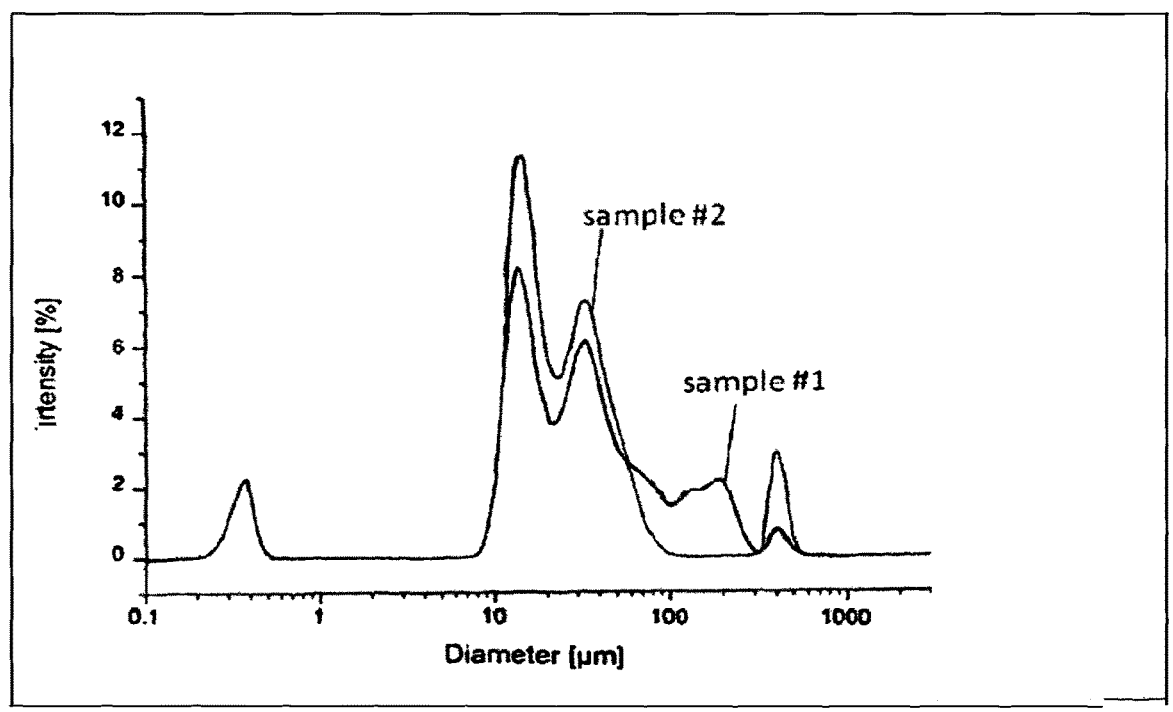
FIG. 5 shows the particle size distribution of spray-dried 2'-fucosyllactose according to the present invention (sample #1 and sample #2) determined by laser diffraction.

FIG. 5 shows the particle size distribution of spray-dried 2'-fucosyllactose according to the present invention (sample #1 and sample #2) determined by laser diffraction. A mean particle size of approx. 68 μm was determined for sample #1. Sample #2 had a mean particle size of approx. 44 μm. Both values are considered to be high for a spray-dried product.

Figure 6:
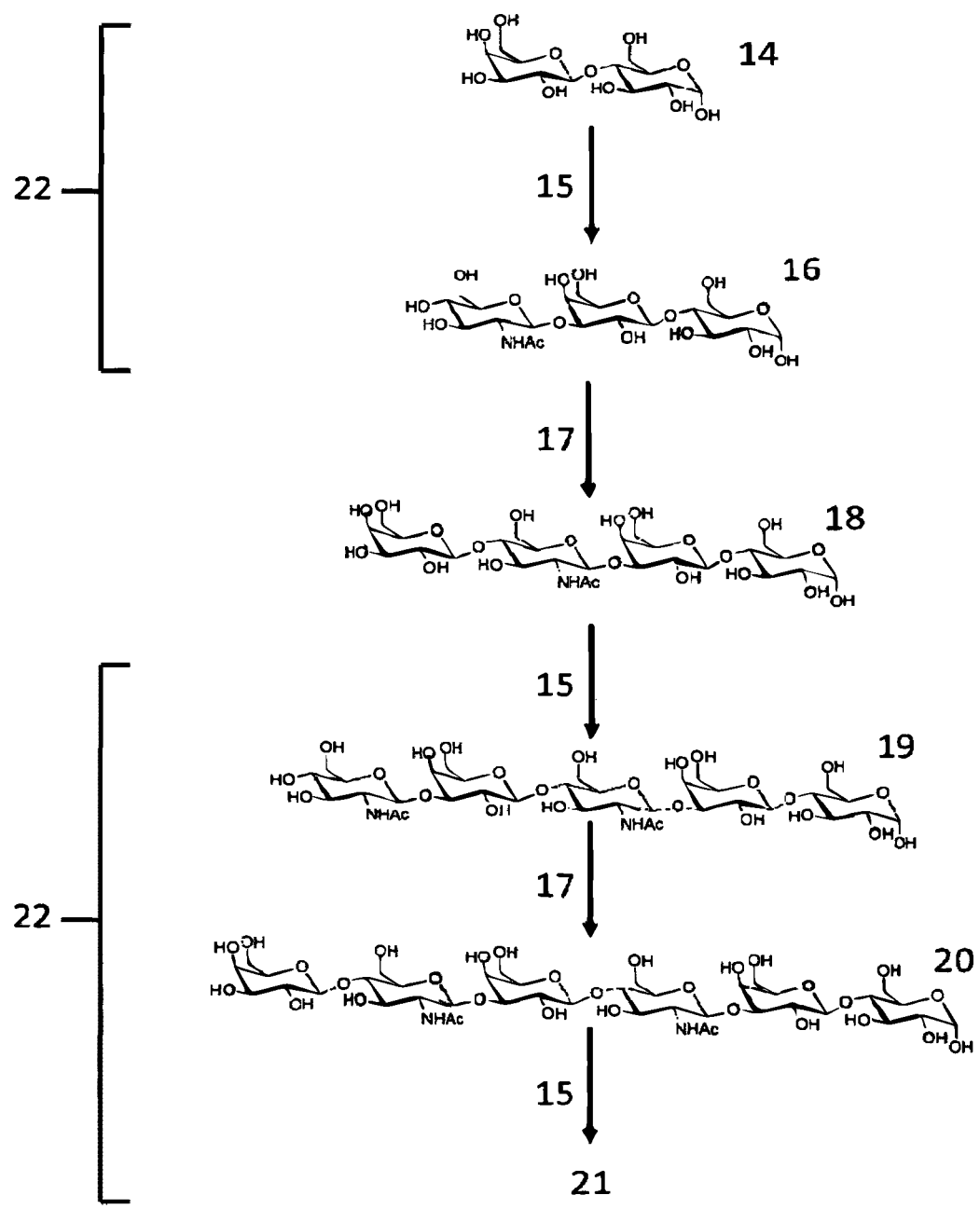
FIG. 6 shows the biosynthesis of the neutral human milk tetrasaccharide lacto-N-neotetraose 17.

FIG. 6 shows the biosynthesis of the neutral human milk tetrasaccharide lacto-N-neotetraose 17. The biosynthesis starts with the disaccharide lactose 14 which is converted by β-1,3-N-acetyl-glucosamintransferase 15 to the trisaccharide lacto-N-triose 16. The trisaccharide lacto-N-triose 16 is subsequently converted into the tetrasaccharide lacto-N-neotetraose 18 by the enzyme 1,4-galactosyltransferase 17. In vivo, a certain percentage of lacto-N-neotetraose 18 is further converted into larger oligosaccharides 19, 20, 21 by the enzymes β-1,3-N-acetyl-glucosamintransferase 15 and 1,4-galactosyltransferase 17. If the aim of the inventive process is the purification of lacto-N-neotetraose 17, the larger oligonucleotides as well as the smaller oligonucleotides (educts) lactose 14 and lacto-N-triose 16 may be present as contaminants 22 in a crude solution containing lacto-N-neotetraose 17. The inventive process enables efficient removal of said contaminants 22.

Figure 7:
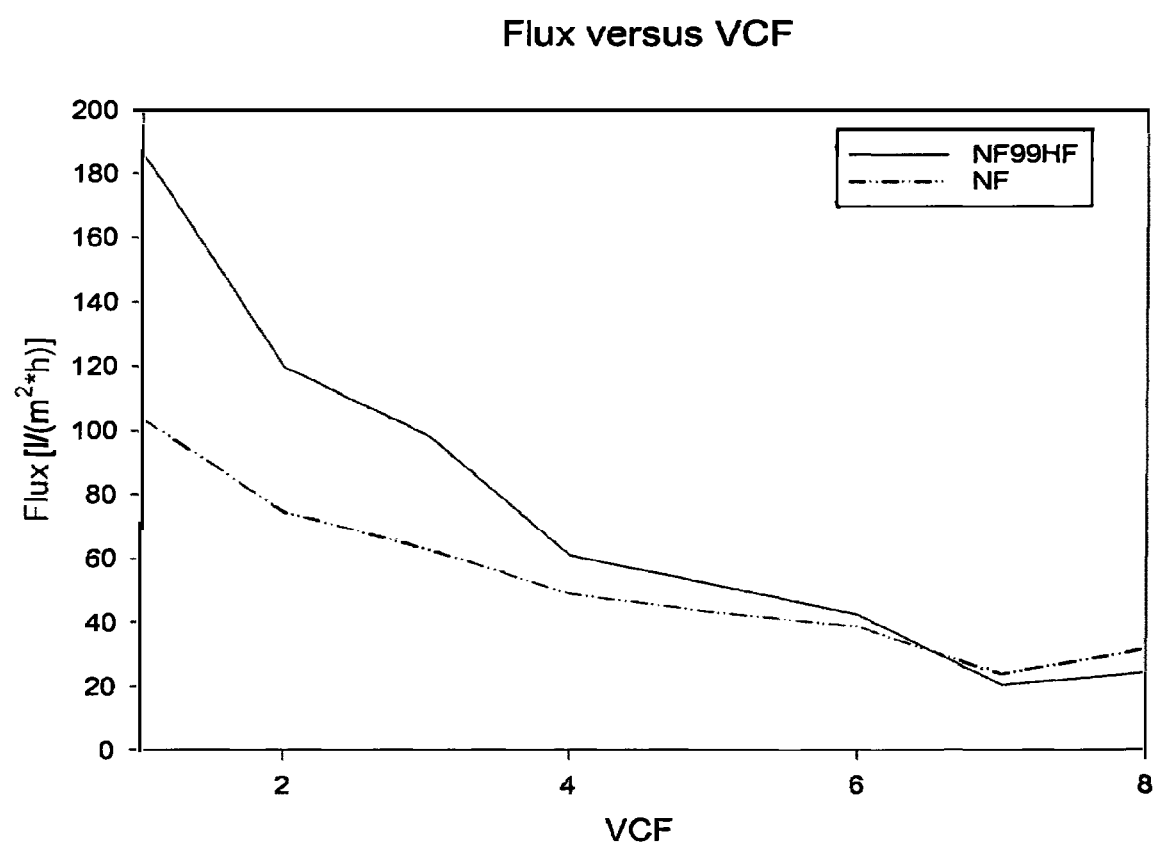
FIG. 7 shows a comparison of two different nanofiltration membranes for the concentration of a 2'-Fucosyllactose containing solution by nanofiltration.

FIG. 7 shows a comparison of two different nanofiltration membranes for the concentration of a 2'-Fucosyllactose containing solution by nanofiltration (VCF: volumetric concentration factor, Flux: expresses the rate at which water permeates the nanofiltration membrane). Alfa Laval nanofiltration membrane type NF99 (NF) and Alfa Laval nanofiltration membrane type NF99HF were used as nanofiltration membrane. It can be seen that at VCF≤6, the NF99HF nanofiltration membrane allows a higher flux, i.e. a faster concentration of the solution.

Figure 8:
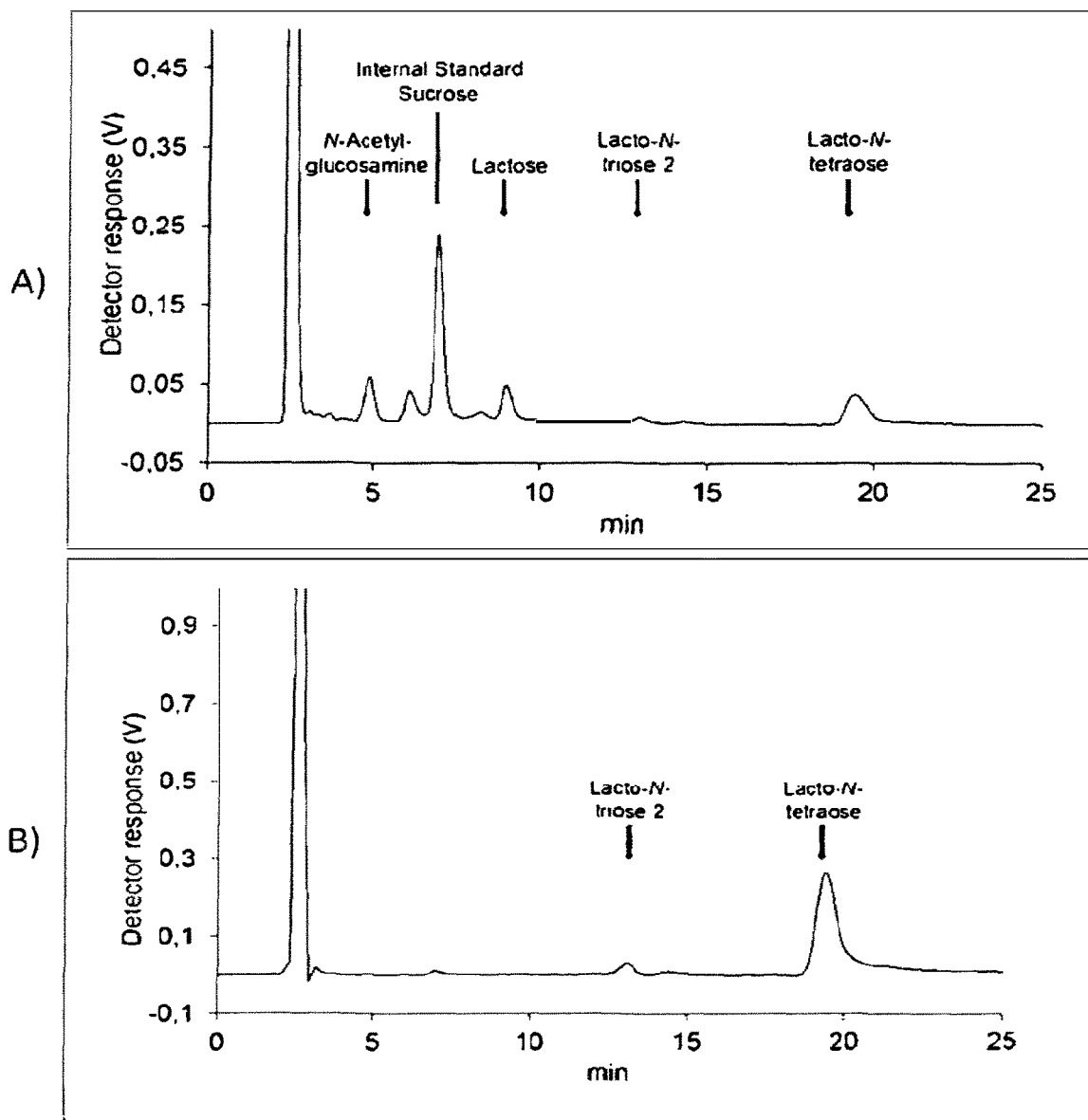
FIG. 8 shows the HPLC analysis of the feed (FIG. 8A) and raffinate (FIG. 8B) of the SMB chromatography of Example 6.

FIG. 8 shows the HPLC analysis of the feed (FIG. 8A) and raffinate (FIG. 8B) of the SMB chromatography of Example 6 (saccharose was used as internal standard; see FIG. 8A). As analytical column, a ReproSil Carbohydrate column (amino functionalized silica column; 5 μm; 250×4.6 mm; Dr. Maisch GmbH; Ammerbuch) was employed with a flow rate of 1.4 ml/min. As eluent, a mixture of acetonitrile and water (68 vol.-%:32 vol.-%) was used. Elution was isocratic. The injection volume was 20 μl. Oven temperature was 35° C. In the SMB chromatography, a strong cationic exchange resin was used which was present in the $H^+$-form.

Figure 9:
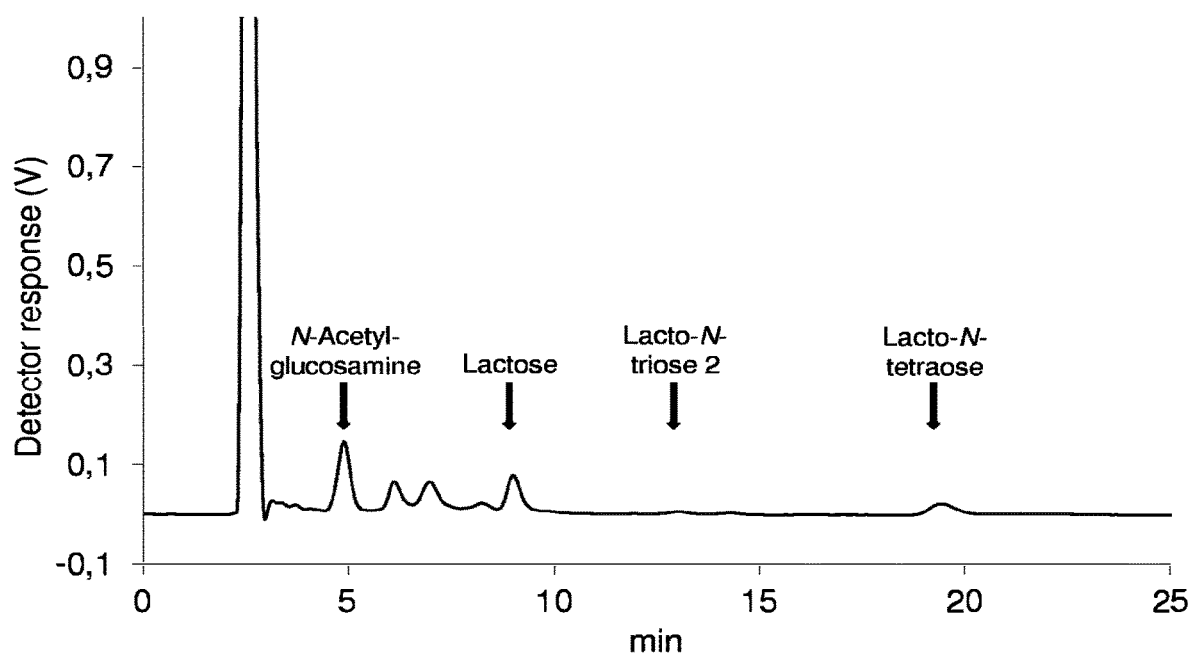
FIG. 9 shows the HPLC analysis of the extract of the SMB chromatography of Example 6.

FIG. 9 shows the HPLC analysis of the extract of the SMB chromatography of Example 6. As analytical column, a ReproSil Carbohydrate column (amino functionalized silica column; 5 μm; 250×4.6 mm; Dr. Maisch GmbH; Ammerbuch) was employed with a flow rate of 1.4 ml/min. As eluent, a mixture of acetonitrile and water (68 vol.-%:32 vol.-%) was used. Elution was isocratic. The injection volume was 20 μl. Oven temperature was 35° C. In the SMB chromatography, a strong cationic exchange resin was used which was present in the H⁺-form.

Figure 10:
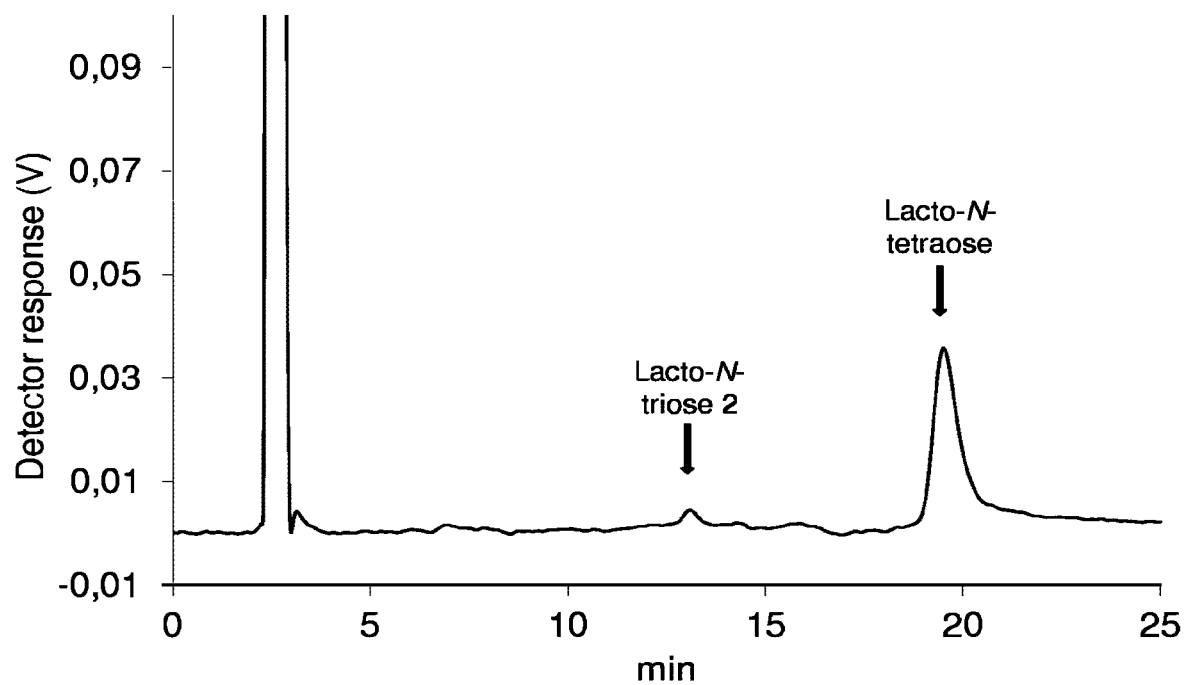
FIG. 10 shows the HPLC analysis of the extract of the second SMB chromatography (=further SMB chromatography according to the invention) of Example 6.

FIG. 10 shows the HPLC analysis of the extract of the second SMB chromatography (=further SMB chromatography according to the invention) of Example 6. As analytical column, a ReproSil Carbohydrate column (amino functionalized silica column; 5 μm; 250×4.6 mm; Dr. Maisch GmbH; Ammerbuch) was employed with a flow rate of 1.4 ml/min. As eluent, a mixture of acetonitrile and water (68 vol.-%:32 vol.-%) was used. Elution was isocratic. The injection volume was 20 μl. Oven temperature was 35° C. In the SMB chromatography, a strong cationic exchange resin was used which was present in the H⁺-form.

Figure 11:
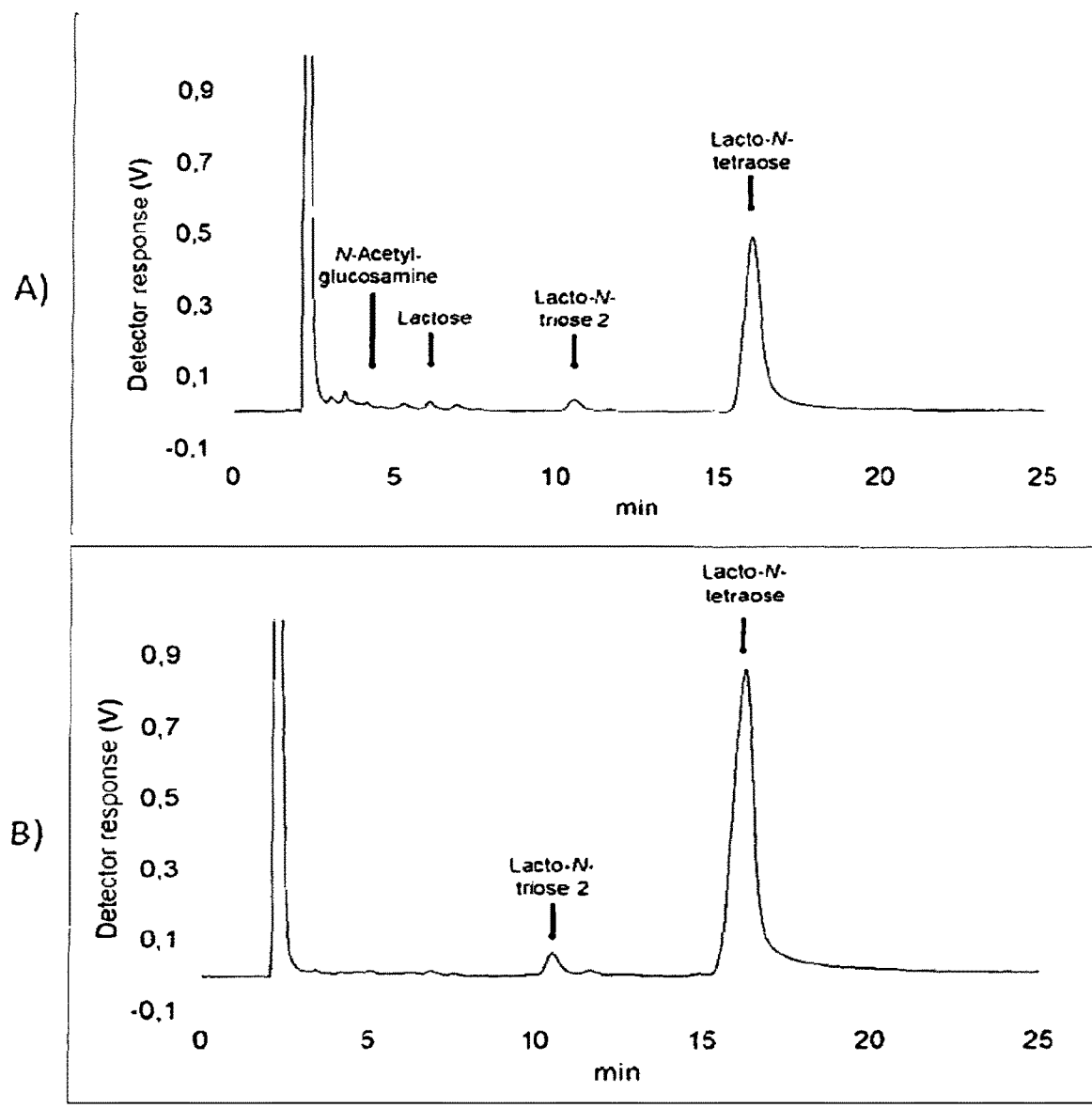
FIG. 11 shows the HPLC analysis of the feed (FIG. 11A) and raffinate (FIG. 11B) of the SMB chromatography of Example 7.

FIG. 11 shows the HPLC analysis of the feed (FIG. 11A) and raffinate (FIG. 11B) of the SMB chromatography of Example 7. As analytical column, a ReproSil Carbohydrate column (amino functionalized silica column; 5 μm; 250×4.6 mm; Dr. Maisch GmbH; Ammerbuch) was employed with a flow rate of 1.4 ml/min. As eluent, a mixture of acetonitrile and water (68 vol.-%:32 vol.-%) was used. Elution was isocratic. The injection volume was 20 μl. Oven temperature was 35° C. In this SMB chromatography, a strong cationic exchange resin was used which was present in the $Ca^{2+}$-form.

Figure 12:
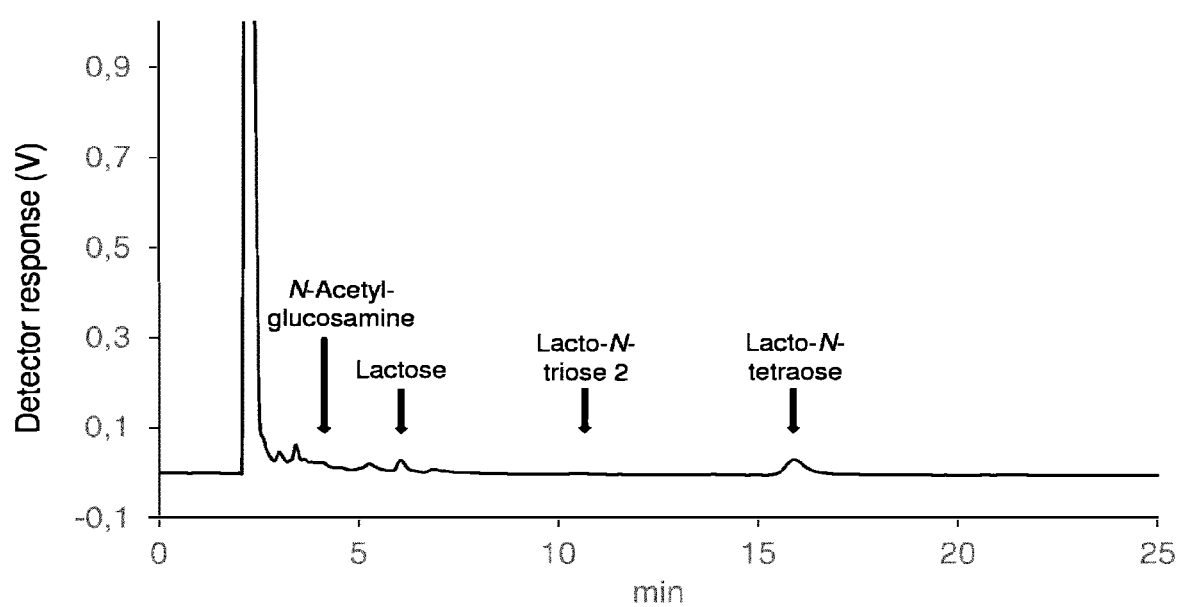
FIG. 12 shows the HPLC analysis of the extract of the SMB chromatography of Example 7.

FIG. 12 shows the HPLC analysis of the extract of the SMB chromatography of Example 7. As analytical column, a ReproSil Carbohydrate column (amino functionalized silica column; 5 μm; 250×4.6 mm; Dr. Maisch GmbH; Ammerbuch) was employed with a flow rate of 1.4 ml/min. As eluent, a mixture of acetonitrile and water (68 vol.-%:32 vol.-%) was used. Elution was isocratic. The injection volume was 20 μl. Oven temperature was 35° C. In this SMB chromatography, a strong cationic exchange resin was used which was present in the $Ca^{2+}$-form.

EXAMPLE 1: PURIFICATION OF 2'-FUCOSYLLACTOSE USING SIMULATED MOVING BED CHROMATOGRAPHY (SMB CHROMATOGRAPHY)

A clear, particle-free solution containing 2'-fucosyllactose at a concentration of 250 g/L was electrodialysed to 0.5 mS/cm using a PC-Cell BED 1-3 electrodialysis apparatus (PC-Cell, Heusweiler, Germany) equipped with PC-Cell E200 membrane stack. Said stack comprised the following membranes: cation exchange membrane CEM: PC SK and the anion exchange membrane AEM:PcAcid60 having a size exclusion limit of 60 Da.

For SMB purification, the 2'-fucosyllactose solution was concentrated to 300 g/L employing a vacuum concentrator at 40° C. For the SMB chromatography, a closed loop SMB system equipped with 12 columns (Prosep® columns with the dimensions: 40 mm×740 mm (Latek, Eppelheim, Germany)) arranged in 4 zones was employed. Each column comprised 760 g of Purolite® PCR833H+(Purolite, Ratingen, Germany) strong cation ion exchanger resin.

The system was operated at a temperature of 25° C. with the following set flow parameters: flow rate zone I was 30.00 ml/min, flow rate zone II was set to 21.00 ml/min, flow rate zone III was 21.48 ml/min, flow rate of zone IV was set to 18.44 ml/min, feed was set to 3.00 ml/min, eluent flow was set to 11.56 ml/min and switching time was set to 17.92 min. As eluent, water with 10% (v/v) food grade ethanol was used.

Major contaminants such as lactose, monosaccharides such as fucose, glucose, galactose and glycerol, were fractioned into the extract. 2'-fucosyllactose and larger oligosaccharide contaminants (e.g. difucosyllactose) were fractioned into the raffinate.

The 2'-fucosyllactose was marginally diluted through the SMB purification step—the concentration of 2'-fucosyllactose in the raffinate was determined at 200 g/l. The pH of the raffinate was adjusted to pH 7 by using 0.2 N NaOH. At the described settings the SMB systems could be continuously operated for at least 3 months.

Then, the obtained solution was again subjected to electrodialysis until a conductivity of less than 0.5 mS/cm was obtained and concentrated to obtain a 40% (w/v) 2'-fucosyllactose solution.

The solution was then subjected to sterile filtration and endotoxin removal by passing the solution through a 3 kDa filter (Pall Microza ultrafiltration hollow fiber module SEP-2013, Pall Corporation, Dreieich).

Using this protocol 2'-fucosyllactose with a purity of 90.4% could be obtained. Major contaminants were 3'-fucosyllactose (2.6%), difucosyllactose (1.5%) and lactose (1.4%). The yield of the purification was approximately 80%.

EXAMPLE 2: PURIFICATION OF 2'-FUCOSYLLACTOSE USING MULTICOMPONENT SMB CHROMATOGRAPHIC SEPARATION

A clear, particle-free solution comprising 2'-fucosyllactose at a concentration of 250 g/L was electrodialysed to 0.5 mS/cm using a PC-Cell BED 1-3 electrodialysis apparatus (PC-Cell, Heusweiler, Germany) equipped with PC-Cell E200 membrane stack. Said stack comprised the following membranes: cation exchange membrane CEM:Pc SK and anion exchange membrane AEM:Pc Acid 60 which possess a size exclusion limit of 60 Da.

For SMB purification, the 2'-fucosyllactose solution was concentrated to 300 g/L employing a vacuum concentrator at 40° C. For the SMB chromatography, a close loop multicomponent SMB System equipped with 24 columns (Prosep® columns with the dimensions: 40 mm×740 mm (Latek, Eppelheim, Germany)) arranged in 2×4 zones was employed. Each column contained 760 g of Purolite® PCR833H+(Purolite, Ratingen, Germany) strong cation ion exchanger resin.

The system was operated at 25° C. with the following set flow parameters: flow rate zone Ia was 30.00 ml/min, flow rate zone IIa was set to 21.00 ml/min, flow rate of zone IIIa was set to 21.48 ml/min, flow rate of zone IVa was set to 18.44 ml/min, feed was set to 3.00 ml/min, eluent flow was set to 11.56 ml/min and switching time was set to 17.92 min.

The raffinate of the first separation was passed on at a flow rate of 3.04 ml/min to a second separation step. The flow rate of zone Ib was kept at 30 ml/min, flow rate of zone IIb was set to 19.61 ml/min, flow rate of zone IIIb was set to 21.63 ml/min, flow rate of zone IVb was set to 18.46 ml/min, eluent flow was set similarly to 11.56 ml/min and switching time of zones Ib to IVb was 10.46 min.

As eluent water with 10% (v/v) food grade ethanol was used.

In the multicomponent separation, contaminants such as lactose, monosaccharides such as fucose, glucose, galactose and glycerol were found in the extract of the first separation step and larger oligosaccharide contaminants (e.g. difucosyllactose) were fractioned into the raffinate of the second separation step.

2'-fucosyllactose was fractioned into the raffinate of the first separation step and the extract of the second separation step and was thus free of low and high molecular weight contaminants. 2'-fucosyllactose was only marginally diluted through the SMB purification step—the concentration of 2'-fucosyllactose in the extract of the second purification step was determined at 200 g/l.

The pH of the raffinate after the first separation step was adjusted to pH 7 by using 0.2 N NaOH.

Using this protocol, 2'-fucosyllactose with a purity of 93.0% could be obtained. Major contaminants were 3'-fucosyllactose (1.1%), difucosyllactose (0.9%) and lactose (1.0%).

EXAMPLE 3: OBTAINING 2'-FUCOSYLLACTOSE IN SOLID FORM BY SPRAY DRYING

The 2'-fucosyllactose fractions obtained by SMB chromatography were again subjected to electrodialysis treatment until a conductivity of less than 0.5 mS/cm was obtained. The fractions were then concentrated under vacuum to obtain 2'-fucosyllactose fractions containing 40% (w/v) 2'-fucosyllactose. The solutions were subsequently subjected to sterile filtration and endotoxin removal by passing the solution through a 3 kDa filter (Pall Microza ultrafiltration hollow fiber module SEP-2013, Pall Corporation, Dreieich, Germany).

The thus-obtained sterile 2'-fucosyllactose solutions were then spray dried using a NUBILOSA LTC-GMP spray dryer (NUBILOSA, Konstanz, Germany). For spray-drying of the 2'-fucosyllactose, the 40% (w/v) solution was passed under pressure through the spray dryer nozzles with an inlet temperature set to 130° C. The flow was adjusted to maintaining an outlet temperature between 66° C. to 67° C.

Using these settings a spray dried powder with less than 5% moisture could be obtained. The moisture contents were determined by Karl-Fischer titration.

EXAMPLE 4: CHARACTERISATION OF THE SPRAY-DRIED 2'-FUCOSYLLACTOSE

1. Differential Scanning Calorimetry (DSC)

A Mettler Toledo 821e (Mettler Toledo, Giessen, Germany) was used to determine thermal events of two samples (sample #1 and sample #2) of spray-dried 2'-fucosyllactose.

Approximately 25 mg of a spray-dried sample was analyzed in crimped Al-crucibles (Mettler Toledo, Giessen, Germany). The samples were cooled to 0° C. at 10 K/min and reheated to 100° C. at a scanning rate of 10 K/min. After cooling down the samples to 0° C. in a second heating cycle the samples were heated to 150° C. The midpoint of the endothermic shift of the baseline during the heating scan was taken as Tg. Exothermic and endothermic peaks are reported by means of the peak temperature and the normalized energy of the event. The results of the DSC analysis of the samples are summarized in Table 1.

TABLE 1

| | | 1$^{st}$ heating scan | | | | 2$^{nd}$ heating scan | | |
|---|---|---|---|---|---|---|---|---|
| | Tg | Endotherm | | exotherm | | Tg1 | Tg2 | exotherm |
| sample | ° C. | ° C. | J/g | ° C. | J/g | ° C. | ° C. | ° C. | J/g |
| #1 | 63.9 | 87.9 | −0.5 | 82.8 | 0.7 | 67.4 | 122.6 | n.d. | n.d. |
| #2 | 87.1 | n.d. | n.d. | n.d. | n.d. | 84.6 | n.d. | 125.9 | 1.1 | n.d.: not detected

DSC analysis of the sample #1 revealed a main glass transition (Tg) at 67.4° C. in the 2$^{nd}$ heating scan. A small second Tg was also detected at 122.6° C. in the 2$^{nd}$ heating scan. The main glass transition was detected in the first 1$^{st}$ heating scan followed by an exo- and endothermic event at temperatures above the Tg. These events are attributed to relaxation effects in the sample.

DSC analysis of the sample #2 showed a substantial higher glass transition (Tg) at 84.6° C. in the 2$^{nd}$ heating scan which was also detected in the 1$^{st}$ heating scan. This may point to a lower residual water content of sample #2 compared to sample #1. Since the glass transition was detected close to the final temperature of the 1$^{st}$ heating scan, potential relaxation phenomena could not be detected. In this sample, a second glass transition could not be detected although a small exothermic peak at 125.9° C. was visible in the 2$^{nd}$ heating scan.

2. X-Ray Powder Diffraction

Wide angle X-ray powder diffraction (XRD) was used to study the morphology of the samples #1 and #2. The X-ray diffractometer Empyrean (Panalytical, Almelo, The Netherlands) equipped with a copper anode (45 kV, 40 mA, K$_{\alpha 1}$ emission at a wavelength of 0.154 nm) and a PIXcel3D detector was used. Approximately 100 mg of the spray-dried samples was analyzed in reflection mode in the angular range from 5-45° 2θ, with a step size of 0.04° 2θ and a counting time of 100 seconds per step.

XRD analysis of samples #1 and #2 revealed the fully amorphous state of both samples and showed no characteristic peaks of crystalline matter (see FIG. 4 for an overlay of both diffractograms).

3. Laser Diffraction

Laser-diffraction measurements were performed using a Partica LA-950 Laser Diffraction Particle Size Distribution Analyzer (Horiba, Kyoto, Japan) equipped with a 605 nm laser diode for detecting particles >500 nm and 405 nm blue light emitting diode (LED) for detecting particles <500 nm. Isooctane was used as dispersion medium (refractive index of 1.391). Since the refractive index of the samples was unknown, the refractive index of sugar (disaccharide) particles was used (1.530). The samples were dispersed in isooctane by ultrasonication for up to 5 minutes. Prior to measurement, the system was blanked with isooctane. The dispersion of each sample was measured 3 times and the mean values and the standard deviation are reported.

The mean particle size (weighted average of particle sizes by volume) and the mode particle size (peak of the distribution) were recorded. In addition to the particle distribution by volume (q %), the result were recorded as:

d(v, 10): particle diameter corresponding to 10% of the cumulative un dersize distribution by volume d(v, 50): particle diameter corresponding to 50% of the cumulative un dersize distribution by volume d(v, 90): particle diameter corresponding to 90% of the cumulative un dersize distribution by volume The particle size distribution for sample #1 and #2 is shown in FIG. 5. The mode size, which represents the particle size of the highest intensity, is comparable for both samples. Overall, the mean particle size of 67.85 μm (sample #1) and 43.65 μm (sample #2), respectively, is regarded as unusually high for spray-dried particles. The fraction detected at higher particle diameters is probably caused by agglomerated powder particles.

Table 2 summarizes the particles size characteristics of sample #1 and #2.

TABLE 2

| Size | sample #1 | sample #2 |
| --- | --- | --- |
| Mean [µm] | 67.84 ± 38.12 | 43.65 ± 0.57 |
| Mode [µm] | 12.60 ± 0.07 | 13.92 ± 0.01 |
| D10 [µm] | 10.39 ± 0.17 | 10.65 ± 0.01 |
| D50 [µm] | 25.67 ± 4.41 | 19.68 ± 0.03 |
| D90 [µm] | 68.13 ± 26.30 | 52.37 ± 0.76 |

EXAMPLE 5: VOLUME REDUCTION AND DESALTING OF 2'-FUCOSYLLACTOSE COMPRISING SUPERNATANT USING NANOFILTRATION

For the concentration and desalting of 2'-fucosyllactose containing culture supernatant, an Alfa Laval M-20 membrane filtration module equipped with either a NF99 (Alfa Laval NF99) or NF99HF (Alfa Laval NF99HF) nanofiltration membrane was employed. The used 2'-fucosyllactose containing culture supernatant (containing 25 g/l 2'-fucosyllactose) was separated from the fermentation microbial biomass by using cross-flow filtration. The molecular cut-off of the cross-flow filtration membrane was 150 kDa (Strass-Burger Filter Micro Cross Module® FS10LFC-FUS1582).

The cell free filtrate was then treated with cation ion exchanger (Lewatit S2568 in proton form (Lanxess)) and anion ion exchanger (Lewatit S6368 in carbonate form (Lanxess)) before being subject to nanofiltration. The solution was neutralized after each ion exchanger step using sodium hydroxide solution or hydrochloric acid, respectively. Inlet pressure of the membrane module was 42 bar and outlet pressure was 40 bar, flow rate of the feed within the membrane module was 8 liter/min. The permeate was removed from the process, whereas the retentate was fed back into reservoir and membrane module. The volume of the reservoir connected to the membrane stack was 6 liters. During the concentration of the 2'-fucosyllatose-comprising solution the reservoir was continuously filled with 2'-fucosyllactose culture supernatant solution until an 8-fold concentrated solution was obtained.

FIG. 7 shows the obtained flux (L/m$^2$/h) plotted against the volume concentration factor (VCF) of the two employed membranes. Having concentrated the 2'-fucosyllactose concentration 8-fold to approximately 200 g/l 2'-fucosyllactose, the concentrated solution was diafiltered for desalting by adding deionized water at the same rate as permeate was obtained from the membrane module. Using the diafiltration step, the conductivity of the 2'-fucosyllactose concentrate could decrease from 25 mS to less than 7 mS using the HF99HF membrane.

By using this nanofiltration approach, the 2'-fucosyllactose solution could be concentrated 8-fold to a 2'-fucosyllactose concentration of ≥200 g/l 2'-fucosyllactose under mild conditions (avoiding thermal exposure), with the diafiltration step a large fraction of the salt content could be removed. The 2'-fucosyllactose concentrate was subjected to electrodialysis for further reduction of the salt content.

EXAMPLE 6: PURIFICATION OF LACTO-N-TETRAOSE USING TWO SIMULATED MOVING BED CHROMATOGRAPHY STEPS AND AN ION EXCHANGER RESIN IN H$^+$ FORM

A clear particle free lacto-N-tetraose solution (30 g/l) obtained from bacterial fermentation was electrodialysed to a conductivity of 0.5 mS/cm using a PC-Cell electrodialysis apparatus (see above). For SMB chromatography, the lacto-N-tetraose solution was concentrated to 50 g/l under vacuum at 40° C. Alternatively, the lacto-N-tetraose containing solution can be desalted and concentrated using a nanofiltration membrane (e.g. nanofiltration membrane HF99HF from Alfa Laval).

For SMB chromatography, a closed loop SMB system equipped with 12 columns (Prosep® glas columns with the dimensions: 40 mm×740 mm (Lartek, Eppelheim, Germany) arranged in 4 zones was employed. Each glass column contained 760 g of Purolite® PCR833H$^+$ strong cation ion exchanger resin. The strong cationic exchanger resin was present in the H$^+$-form.

The system was operated at 25° C. with the following parameter settings: flow rate of zone I was set to 30.00 ml/min, flow rate of zone II was set to 19.07 ml/min, the flow rate of zone IV was set to 18.44 ml/min. Feed was kept at 1 ml/min and eluent flow was set to 11.56 ml/min with a switching time of 17.92 min. As eluent water with 10% (v/v) food grade ethanol was used.

Under these parameters, the lacto-N-tetraose and larger neutral oligosaccharides were fractioned into the raffinate. The purity of lacto-N-tetraose was 86.3% instead of 33.4% at the SMB feed (see FIG. 7A for HPLC analysis of the SMB feed and FIG. 7B for HPLC analysis of the SMB raffinate). Contaminants such as lactose, monosaccharides and glycerol were found in the SMB extract fraction (see FIG. 8 for HPLC analysis of the SMB extract fraction). The raffinate containing the lacto-N-tetraose was adjusted to neutral pH using a 0.2 N NaOH solution.

The pH of the obtained extract containing the lacto-N-tetraose was adjusted to pH 7 by using 0.2 N NaOH. Then, the obtained solution was subjected to electrodialysis until a conductivity of less than 0.5 mS was again obtained. The solution was then concentrated under vacuum to approx. 50 g/l lacto-N-tetraose and then sterile-filtered by passing through a 3 kDa cross-flow filter (Pall Microza ultrafiltration hollow fiber module SEP-2013, Pall Corporation, Dreieich).

In order to separate away larger oligosaccharide contaminants from the lacto-N-tetraose, a second SMB chromatography separation was performed. Using the same SMB system the parameters were changed as follows: flow rate zone I 30 ml/min, flow rate zone II 19.27 ml/min, flow rate zone IV 17.30 ml/min. Feed was set to 2.08 ml/min and eluent flow 12.70 ml/min. Raffinate flow was 4.04 ml/min and extract flow was 10.73 ml/min. Switching time of the SMB separation was set to 10.46 min. As eluent again a water/ethanol mixture 9:1 (v/v) was employed. The HPLC analysis of the extract of the second lacto-N-tetraose separation by SMB chromatography is shown in FIG. 10.

Under these conditions, the lacto-N-tetraose was fractioned into the extract and 5 to 10% of the total amount of larger neutral oligosaccharides was found in the raffinate. Using this protocol (amino functionalized silica column after second SMB step), lacto-N-tetraose with a purity of 93.1% could be obtained.

EXAMPLE 7: PURIFICATION OF LACTO-N-TETRAOSE USING SIMULATED MOVING BED CHROMATOGRAPHY WITH AN ION EXCHANGER RESIN IN CA$^{2+}$ FORM

A clear particle free lacto-N-tetraose solution (30 g/l) obtained from bacterial fermentation was electrodialysed to a conductivity of 0.5 mS/cm using a PC-Cell electrodialysis apparatus (see above).

For SMB chromatography with calcium as counter-ion, the lacto-N-tetraose solution was concentrated to 50 g/l under vacuum at 40° C. For SMB chromatography a close loop SMB system equipped with 12 columns (Prosep® glas columns with the dimensions: 40 mm×740 mm (Lartek, Eppelheim, Germany)) arranged in 4 zones was employed.

Each column contained 760 g of Purolite® PCR833H+ strong cationic ion exchanger resin. The cationic ion exchanger resin was washed with 50 Liter of a 200 mM $CaCl_2$) to exchange the $H^+$ ions by $Ca^{2+}$ ions. Thus, the strong cationic exchanger resin was present in the $Ca^{2+}$-form.

The system was operated at 25° C. with the following parameter settings: flow rate zone I was set to 30.00 ml/min, flow rate of zone II was set to 20.07 ml/min, the flow rate of zone IV was set to 17.04 ml/min. Feed was kept at 2.5 ml/min and eluent flow was set to 11.56 ml/min with a switching time of 17.92 min. As eluent water with 10% (v/v) food grade ethanol was used.

EXAMPLE 8: OBTAINING LACTO-N-TETRAOSE IN SOLID FORM BY SPRAY DRYING

Fractions containing lacto-N-tetraose were concentrated under vacuum to obtain a lacto-N-tetraose concentration of 25% (w/v). The solutions were then for sterile filtration and endotoxin removal passed through a 3 kDa filter (Pall Microza ultrafiltration hollow fiber module SEP-1013, Pall Corporation, Dreieich, Germany).

The thus-obtained sterile lacto-N-tetraose solution was then spray dried using a Mini Spray Dryer B-290 (Büchi Labortechnik GmbH, Essen, Germany). For the spray-drying of the lacto-N-tetraose, the solution was passed under pressure through the spray dryer nozzles with an outlet temperature between 120° C. and 130° C. and flow was adjusted to maintaining an exhaust temperature between 66° C. to 67° C. Using these settings, a spray-dried powder with 7-9% moisture and a yield of 72% spray dried lacto-N-tetraose could be obtained. The moisture contents were determined by Karl-Fischer titration.

The invention claimed is:

1. A process for the purification of a neutral human milk oligosaccharide from a microbial fermentation solution, comprising:
   before step a) providing a microbial fermentation solution comprising neutral human milk oligosaccharide;
   a) removing biomass and/or insoluble material from the solution;
   b) applying the solution obtained in step a) to at least one of cation exchange chromatography and anion exchange chromatography;
   c) optionally subjecting the solution obtained in step a) or step b) to dialysis or diafiltration;
   d) applying the solution obtained in step a), step b) or step c) to simulated moving bed chromatography;
   e) concentrating the solution obtained in at least one of the preceding steps, and
   f) spray-drying the solution from step e).

2. The method of claim 1, wherein electrodialysis is used for the dialysis in step c) and is performed.

3. The method of claim 1, wherein nanofiltration is used for the diafiltration in step c) and is performed.

4. The method of claim 1, wherein evaporation, nanofiltration, or reverse osmosis is used for the concentrating in step e).

5. The method of claim 4, wherein the concentrating step e) results in a concentration of neutral human milk oligosaccharide of about 50 g/L to about 300 g/L.

6. The method of claim 5, wherein the concentrating step e) results in a concentration of neutral human milk oligosaccharide of about 100 g/L to about 200 g/L.

7. The method of claim 4, wherein evaporation is used for the concentrating in step e).

8. The method of claim 4, wherein nanofiltration is used for the concentrating in step e).

9. The method of claim 4, wherein reverse osmosis is used for the concentrating in step e).

10. The method of claim 1, wherein cross-flow filtration is used for the separating in step a).

11. The method of claim 1, wherein both cation and anion exchange chromatography are performed at step b).

12. The method of claim 1, further comprising sterile-filtering the purified solution obtained after step e).

13. The method of claim 1, wherein the neutral human milk oligosaccharide is selected from the group consisting of 2'-fucosyllactose, 3'-fucosyllactose, 2'3-difucosyllactose, lacto-N-triose II, lacto-N-tetraose, lacto-N-neotetraose, lacto-N-fucopentaose, lacto-N-neofucopentaose I, lacto-N-fucopentaose II, lacto-N-fucopentaose III, lacto-N-fucopentaose V, lacto-N-neofucopentaose V, lacto-N-difucohexaose I, lacto-N-difucohexaose II, 6'-galactosyllactose, 3'-galactosyllactose, lacto-N-hexaose, lacto-N-neohexaose, para-lacto-N-hexaose, para-lacto-N-neohexaose, and difocosyl-lacto-N-neohexaose.

14. The method of claim 12, wherein the neutral human milk oligosaccharide is lacto-N-tetraose or lacto-N-neotetraose.

15. The method of claim 1 wherein wherein electrodialysis is used for the dialysis in step c) and is performed.

16. The method of claim 1, wherein nanofiltration is used for the diafiltration in step c) and is performed.

17. The method of claim 2, wherein evaporation, nanofiltration, or reverse osmosis is used for the concentrating in step e).

18. The method of claim 3, wherein evaporation, nanofiltration, or reverse osmosis is used for the concentrating in step e).

19. The method of claim 1, wherein at least one column used in the simulated moving bed chromatography comprises an ion exchange resin.

20. A process for the purification of a neutral human milk oligosaccharide from a microbial fermentation solution, comprising:
   before step a) providing a microbial fermentation solution comprising neutral human milk oligosaccharide;
   a) removing biomass and/or insoluble material from the solution using filtration;
   b) applying the solution obtained in step a) to ion exchange chromatography;
   c) subjecting the solution obtained in step b) to electrodialysis or nanofiltration;
   d) applying the solution obtained in step c) to simulated moving bed chromatography, wherein at least one column used in the simulated moving bed chromatography comprises a cation exchange resin;
   e) concentrating the solution obtained in at least one of the preceding steps by a method consisting of evaporation, nanofiltration and reverse osmosis; and
   f) spray drying the concentrated solution from step e).

* * * * *